US00PP17720P3

(12) United States Plant Patent
Redman

(10) Patent No.: US PP17,720 P3
(45) Date of Patent: May 15, 2007

(54) ***CHRYSANTHEMUM* PLANT NAMED 'MEGA TIME YELLOW'**

(50) Latin Name: *Chrysanthemum morifolium*
Varietal Denomination: Mega Time Yellow

(75) Inventor: Ruth Redman, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 213 days.

(21) Appl. No.: 11/146,389

(22) Filed: Jun. 6, 2005

(65) Prior Publication Data

US 2006/0037120 P1 Feb. 16, 2006

Related U.S. Application Data

(60) Provisional application No. 60/602,277, filed on Aug. 16, 2004.

(51) Int. Cl.
*A01H 5/00* (2006.01)

(52) U.S. Cl. ..... Plt./295

(58) Field of Classification Search ..... Plt./295
See application file for complete search history.

(56) References Cited

U.S. PATENT DOCUMENTS

| | | | |
|---|---|---|---|
| PP15,194 P3 | 9/2004 | Redman | Plt./295 |
| PP15,463 P3 | 1/2005 | Redman | Plt./295 |

*Primary Examiner*—Kent Bell
*Assistant Examiner*—Annette H Para
(74) *Attorney, Agent, or Firm*—Winston & Strawn, LLP

(57) ABSTRACT

A new variety of *Chrysanthemum* plant named 'Mega Time Yellow,' having medium size, yellow single flowers with a small dark brown spot in the center of a lime green disc. The new variety has a medium vigor with a free branching uniform habit and a good foliage presentation.

1 Drawing Sheet

Latin name of the genus and species: Botanical classification: *Chrysanthemum morifolium.*

Variety denomination: The new *Chrysanthemum* variety denomination is 'Mega Time Yellow'.

BACKGROUND OF THE INVENTION

The present invention comprises a new and distinct cultivar of *Chrysanthemum* botanically known as *Chrysanthemum morifolium,* and referred to by the cultivar name 'Mega Time Yellow'.

'Mega Time Yellow', identified as 20929-11 was discovered as a naturally occurring whole plant mutation in a controlled cultivated planting of the variety 'Mega Time Amber' (U.S. Plant Pat. No. 15,194).

The new variety 'Mega Time Yellow' has been asexually reproduced by vegetative cuttings, in Chichester, West Sussex, United Kingdom and the distinguishing characteristics are retained through successive generations of asexual reproduction.

BRIEF SUMMARY OF THE INVENTION

'Mega Time Yellow' is a pot type of *Chrysanthemum* plant variety having bright yellow single flowers with a small brown spot in the middle of a lime green disc.

Comparison with Parent

Plants of the new *Chrysanthemum* variety 'Mega Time Yellow' are similar to the parent 'Mega Time Amber' in plant habit and growth rate. In side-by-side comparisons in Chichester, West Sussex, United Kingdom, under commercial practice, plants of the new *Chrysanthemum* variety 'Mega Time Yellow' differed from plants of the parent 'Mega Time Amber' in the following characteristics:

1. The new variety 'Mega Time Yellow' produces bright yellow single flowers whereas the parent 'Mega Time Amber' produces amber/golden single flowers.
2. Plants of the new variety 'Mega Time Yellow' have a slower response than plants of the parent 'Mega Time Amber'.

Comparison with Swing Time Yellow

Plants of the new *Chrysanthemum* variety 'Mega Time Yellow' are dissimilar to plants of the variety 'Swing Time Yellow' (U.S. Plant Pat. No. 15,463) in plant habit and growth rate. However, in side-by-side comparisons in Chichester, West Sussex, United Kingdom, under commercial practice, plants of the new *Chrysanthemum* variety 'Mega Time Yellow' differed from plants of 'Swing Time Yellow' in the following characteristics:

1. The new variety 'Mega Time Yellow' produces bright yellow single flowers with a small brown spot in the center of the disc whereas 'Swing Time Yellow' produces golden yellow single flowers with a light green disc.
2. Plants of the new variety 'Mega Time Yellow' have smaller and shorter inflorescence than plants of 'Swing Time Yellow'.
3. Plants of the new variety 'Mega Time Yellow' have lighter foliage than plants of 'Swing Time Yellow'.
4. Plants of the new variety 'Mega Time Yellow' have a slower response time than plants of 'Swing Time Yellow'.

BRIEF DESCRIPTION OF ILLUSTRATIONS

Typical specimens of the plant and flowers for the new *Chrysanthemum* variety 'Mega Time Yellow' are shown in the accompanying digital photograph. The colors shown are as true as possible within the usual limits of this kind of illustration.

FIG. 1 is a whole plant view of the new variety 'Mega Time Yellow' grown in a pot. The plant shown in the illustration is 60 days from the onset of Short Days.

DETAILED BOTANICAL DESCRIPTION

The following description of the new *Chrysanthemum* variety 'Mega Time Yellow' is of plants grown in a greenhouse in Chichester, West Sussex, United Kingdom, in the month of June. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as one B9 treatment at about 2 grams per liter to produce a commercial product, the plants may be pinched once with the center bud removed. The typical container size for commercial growth is 1 liter. It has been observed that the shelf life of the new variety is about 28 days with a response time of about 8.5 weeks. The new variety is suitable for growth in a temperature range of about 15° C. to 25° C.

The following description is with respect to a plant produced as pot *Chrysanthemum.* In the description of this new *Chrysanthemum* variety, color values have been taken from The Royal Horticultural Society Colour Chart (R.H.S.C.C.).

Plant

Plant type: Pot.
Habit: Upright and free branching.
Height (cm): 24.
Width (cm): 35.
Stem:
- *Length* (*cm*).—6.5.
- *Diameter* (*cm*).—0.5.
- *Texture.*—Slightly pubescent.
- *Color.*—137B.

Branching characteristics: Upright and free branching.
Lateral branches:
- *Length* (*cm*).—16.
- *Diameter* (*cm*).—0.8.
- *Texture.*—Slightly pubescent.

Number of breaks from pinch: 5.
Response time: About 58 days.
Vigor: Medium.
Shelf life: About 28 days.
Life of blooms: About 28 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of 2.5 gm/liter B9 @2, 21 and 28 days after sticking unrooted cuttings.
The plants were grown for two weeks in Long Day conditions (20 hours of light) and then transferred to Short Day conditions (13 hours of dark).
Propagation:
- *Type.*—Vegetative propagation via stem cuttings.
- *Time to rooting.*—14 days with soil temperatures of 18° C.
- *Rooting habit.*—After 7 Long Days, the first roots emerge and form root primordia. In 14 Long Days, a complete root system is developed.

Foliage

Number of leaves per lateral branch: 12.
Compound or single: Single.
Arrangement of leaves: Alternate.
- *Shape of leaf.*—Typically 5 lobed ovate.
- *Size of leaf.*—Width (cm): 4. Length (cm): 6.
- *Leaf apex.*—Acute.
- *Base.*—Obtuse.
- *Attachment.*—Petioled.
- *Aspect.*—Slightly curving.
- *Margin.*—Palmately lobed.
- *Surface characteristics.*—Top: Slightly pubescent. Bottom: Pubescent.

Petiole:
- *Color.*—137D.
- *Length* (*cm*).—1.5.
- *Diameter* (*cm*).—0.2.
- *Surface.*—Slightly pubescent.

Venation: Net, prominent lateral and mid-veins at underside.
- *Color.*—Upper side: 137C. Under side: 138B.

Color:
- *Mature leaf, upper side.*—137C; under side: 138C.
- *Young leaf, upper side.*—137B; under side: 138C.

Flower

Flower appearance: Matte.
Flower type: Single.
Flower form: Slightly cupped.
Flower shape: Round.
Flowering habit: Cyme.
Number of blossoms per branch: 6.
Typical and observed flowering season: January to December.
Inflorescence form: Cyme.
- *Depth of fully expanded blossoms* (*cm*).—2.
- *Diameter of fully expanded blossoms* (*cm*).—7.

Phyllaries:
- *Number.*—20.
- *Color.*—Near 137C.
- *Length* (*cm*).—0.7.
- *Width* (*cm*).—0.1.
- *Texture/Appearance.*—Pubescent.

Peduncle:
- *Length* (*cm*).—10.
- *Diameter* (*cm*).—0.5.
- *Angle from stem* (*degrees*).—10.
- *Color.*—137C.
- *Surface.*—Pubescent.
- *Habit.*—Slightly curving.
- *Strength.*—Moderately strong.

Pedicel:
- *Length.*—Terminal (cm): 3; lateral (cm): 4.5.
- *Diameter* (*cm*).—0.2.
- *Color.*—137C.
- *Surface.*—Pubescent.

*Habit.*—Slightly curving.
*Strength.*—Moderately strong.

Ray florets:
*Form/Shape.*—Straight with parallel edges to the central mid vein with a rounded tip.
*Texture/appearance.*—Matte.
*Number per flower.*—25.
*Length* (*cm*).—3.5; Width (cm): 1.
*Apex.*—Rounded.
*Base.*—Tapered.
*Margin.*—Entire.

Disc florets:
*Form/shape.*—Cylindric.
*Texture/appearance.*—Shiny.
*Number per flower.*—120.
*Length* (*cm*).—0.6; Width (cm): 0.1.
*Diameter of disc* (*cm*).—1.3.

Fragrance: None.

Flower bud (at onset of color):
*Length* (*cm*).—1.
*Diameter* (*cm*).—1.
*Form/shape.*—Globular.

General flower color:
1. *Ray florets, upper side.*—Immature: 9A. Mature: 5A. Older/Fading: 5B.
2. *Ray florets, under side.*—Immature: 9A. Mature: 5A. Older/Fading: 5B.
3. *Disc florets.*—Immature: 143B and near 152B for disc center. Mature: 9B and near 152B for disc center. Older/Fading: 9B and near 152B for disc center.

6. Bud: 9A.

Flower progression with age: There are no changes to the flower form but there is a slight color fading with age.

Other distinguishing characteristics: Small dark spot in the center of the disc. Color code is near 152B.

Reproductive Organs

Gynoecium present on Ray and Disc florets.

Ray florets per individual flower: Pistillate.
*Pistil number.*—25.
*Stigma color.*—Near 154A.
*Stigma shape.*—Forked.
*Style color.*—Near 154B.
*Style length* (*cm*).—0.2.

Disc florets per individual flower: Pistillate.
*Pistil number.*—Near 130.
*Stigma color.*—Near 154A.
*Stigma shape.*—Forked.
*Style color.*—Near 154B.
*Style length* (*cm*).—0.2.

Androecium not observed.

Fruit and seeds: None observed.

What is claimed is:

1. A new and distinct variety of *Chrysanthemum* plant, substantially as described and illustrated herein.

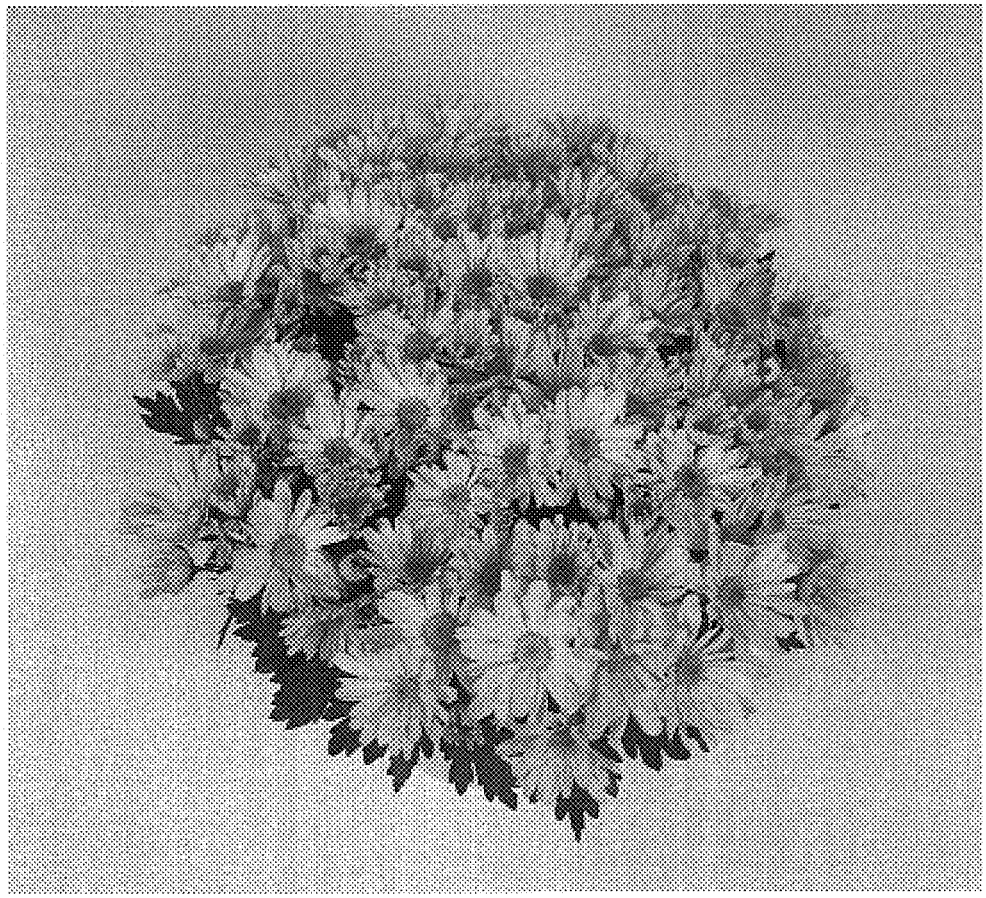

* * * * *